United States Patent [19]
Lentz et al.

[11] Patent Number: 5,843,166
[45] Date of Patent: Dec. 1, 1998

[54] COMPOSITE GRAFT-STENT HAVING POCKETS FOR ACCOMODATING MOVEMENT

[75] Inventors: David J. Lentz, Randolph; Edward Dormier, Rockaway, both of N.J.

[73] Assignee: Meadox Medicals, Inc., Oakland, N.J.

[21] Appl. No.: 784,843

[22] Filed: Jan. 17, 1997

[51] Int. Cl.$^6$ ................................................. A61F 2/06
[52] U.S. Cl. ................................................. 623/1; 623/12
[58] Field of Search ................................ 623/1, 11, 12; 606/194, 195, 198; 600/36

[56] References Cited

U.S. PATENT DOCUMENTS

| | | |
|---|---|---|
| 3,657,744 | 4/1972 | Ersek . |
| 4,300,244 | 11/1981 | Bokros . |
| 4,409,172 | 10/1983 | Ward, Jr. et al. . |
| 4,732,152 | 3/1988 | Wallsten et al. . |
| 5,078,726 | 1/1992 | Kreamer . |
| 5,123,917 | 6/1992 | Lee . |
| 5,282,824 | 2/1994 | Gianturco . |
| 5,330,500 | 7/1994 | Song . |
| 5,366,504 | 11/1994 | Anderson et al. . |
| 5,383,926 | 1/1995 | Lock et al. . |
| 5,387,235 | 2/1995 | Chuter . |
| 5,389,106 | 2/1995 | Tower . |
| 5,456,713 | 10/1995 | Chuter . |
| 5,507,769 | 4/1996 | Marin et al. .................... 623/1 |
| 5,507,771 | 4/1996 | Gianturco . |
| 5,522,881 | 6/1996 | Lentz . |
| 5,562,726 | 10/1996 | Chuter . |
| 5,618,299 | 4/1997 | Khosravi et al. . |

FOREIGN PATENT DOCUMENTS

| | | |
|---|---|---|
| 0 657 147 | 6/1995 | European Pat. Off. . |
| 39 02 364.8 | 8/1989 | Germany . |
| 1457 921 | 2/1989 | U.S.S.R. . |
| WO 95/05132 | 2/1995 | WIPO . |
| WO 95/29647 | 11/1995 | WIPO . |
| WO 96/00103 | 1/1996 | WIPO . |
| WO 96/10967 | 4/1996 | WIPO . |
| WO 96/22745 | 8/1996 | WIPO . |
| WO 96/28115 | 9/1996 | WIPO . |
| WO 96/33672 | 10/1996 | WIPO . |
| WO 96/35577 | 11/1996 | WIPO . |

OTHER PUBLICATIONS

Lawrence, Jr. D.D., Charnsangavej, C., Wright, K.C., Gianturco, C., and Wallace, S., Percutaneous Endovascular Graft: Experimental Evaluation, Radiology 1986; 163:357–360.

*Primary Examiner*—Debra S. Brittingham
*Attorney, Agent, or Firm*—Hoffmann & Baron, LLP

[57] ABSTRACT

An implantable intraluminal device includes a first porous elongate tube with first and second opposed ends and an exterior surface and an interior luminal surface. A radially expandable member is disposed about the exterior surface of the first tube. A second porous elongate tube is disposed concentrically over the first tube and the radially expandable member and is secured to the first tube so that the radially expandable member is transversely mobile within a pocket formed by the securement of the first tube to the second tube.

25 Claims, 4 Drawing Sheets

COMPOSITE GRAFT-STENT HAVING POCKETS FOR ACCOMODATING MOVEMENT

FIELD OF INVENTION

The present invention relates generally to tubular implantable prosthetic devices such as vascular grafts and other endoprostheses. More particularly, the present invention relates to an elongate multilayer tubular graft formed of porous expanded polytetrafluoroethylene (ePTFE) which supports a stent in a pocket created between the layers thereof for longitudinal movement of the stent within the pocket.

BACKGROUND OF THE INVENTION

Intraluminal devices such as grafts and stents are known for treating stenosis, stricture, aneurysms and the like. These devices may be implanted either transluminally in a minimally invasive procedure or may be surgically implanted.

Such intraluminal devices provide a technique for expanding a constricted vessel or for maintaining an open passageway through a vessel. One common technique used to hold open a blocked or constricted vessel, such as a blood vessel, is to employ a vascular stent. Stents are implantable intraluminal devices typically formed of wire which may be radially expanded to hold open constricted vessels. Thus, wire stents are useful to prevent restenosis of a dilated vessel or to eliminate the danger of reocclusion of the vessel. In addition, wire stents can also be used to reinforce various lumen in danger of collapse. However, stents are not generally designed as conduits or bypass devices.

Intraluminal or endoprosthetic grafts, however, are designed as bypass devices which allow fluid flow therethrough. Often, these devices are percutaneously implanted within the vascular system to reinforce collapsing, partially occluded, weakened or abnormally dilated localized sections of, e.g., a blood vessel. Grafts may also be surgically implanted by an anastomosis to replace a badly damaged portion of vessel.

Vascular grafts may be manufactured from a variety of bio-compatible materials. For example, it is well known to use extruded tubes of expanded polytetrafluoroethylene (ePTFE) as vascular grafts. ePTFE is particularly suitable because it exhibits superior biocompatibility. ePTFE tubes may be used as vascular grafts in the replacement or repair of blood vessels because ePTFE exhibits low thrombogenicity. Further, these ePTFE tubes have a microporous structure that allows natural tissue ingrowth and cell endothelialization once implanted into the vascular system. This contributes to long term healing and graft patency.

Grafts formed of ePTFE have a fibrous state which is defined by interspaced nodes interconnected by elongated fibrils. The space between the node surfaces that are spanned by the fibrils is defined as the internodal distance (IND). The art is replete with examples of vascular grafts made of microporous ePTFE tubes useful as vascular grafts. The porosity of an ePTFE vascular graft is controlled by varying the IND of the microporous structure of the tube. An increase in the IND within a given structure results in enhanced tissue ingrowth, as well as, cell endothelialization along the inner surface thereof. Increasing the porosity of the tubular structure, however, reduces the ability of the graft to retain a suture placed therein during implantation. Also, these microporous tubular structures tend to exhibit low axial tear strength. In order to strike an effective balance between porosity and radial strength, multilayer ePTFE tubes have been developed. The porosity of these tubes vary as between the outer and inner layers to achieve a composite structure having sufficient porosity for tissue ingrowth and cell endothelialization while still retaining sufficient radial strength.

It is known in the art to use stents in combination with other endoprostheses, such as, for example, vascular grafts. Stents may be positioned at one or both ends of a graft to support the graft within a portion of the vessel. Thus positioned, the stents help fix the graft to the vessel wall. In addition, stents serve to keep the lumen open and to anchor the graft in place. A single stent may also be employed in combination with a graft to allow the graft to "float" downstream toward the affected vessel. Once properly positioned, the single stent is expanded to anchor the graft in place.

Several techniques for securing one or more stents to a graft are known. For example, hooks or barbs extending from the stent have been used for securing stents to a graft. Alternatively, a stent may be sutured to a graft. Each of these techniques requires either specialized stent attachment means or secondary operations to secure the stents to the graft.

Traditional stents have various shapes and sizes depending upon their intended function. For example, structures which have previously been used as stents include coiled stainless steel springs, helically wound coiled springs manufactured from an expandable heat-sensitive material, expanding stainless steel stents formed of stainless steel wire in a "zig-zag" pattern, cage-like devices made from malleable metal, and flexible tubes having a plurality of separate expandable ring-like scaffold members which permit radial expansion of a graft. Each of these devices is designed to be radially compressible and expandable so that it will easily pass through a blood vessel in a collapsed state and can be radially expanded to an implantable size after the target area of the vessel has been reached. Radial expansion and contraction of each of these causes associated longitudinal expansion and contraction of the stent.

Such expandable stents may be supported between the layers of a multilayer tubular graft. The expandable stent would anchor and support the multilayer tube within the lumen. Upon radial expansion, the stent would hold the graft outwardly against the inner wall of the lumen.

One example of a sleeve-stent combination is shown in U.S. Pat. No. 5,507,771 issued to Gianturco. The sleeve-stent combination shown therein includes one or more spaced apart stents that are interconnected by struts. The stent(s) is/are embedded, glued or stitched to a flexible sleeve (graft).

These embodiments are limited in that the stents are physically immobilized on the surface of or within the sleeve. Thus, when the sleeve-stent device of Gianturco expands radially, shear forces are generated that can result in tearing of the sleeve.

Another example of a graft-stent combination is shown in U.S. Pat. No. 5,123,917 issued to Lee et al. A graft-stent combination shown therein includes a plurality of separate scaffold members (stents) mounted between an inner tube and an outer tube forming the multilayer graft. In one embodiment of this invention, the inner and outer tubes adhere to each other in such a manner that a plurality of separate pockets are formed in which individual scaffold members are immobilized within each pocket. In another embodiment, the scaffold members are adhesively affixed to the outer surface of the inner tube. In yet another embodiment of this invention, a single tube is provided with the scaffold members disposed about either the inner or outer surface of the tube.

These embodiments are limited in that the scaffold members are physically immobilized between both tubes or are secured to one or both of the tubes of the device. In each of these different embodiments, radial expansion of the scaffold member causes a change in the longitudinal expanse thereof. Thus, when the scaffold members expand, shear forces are generated against one or both layers of the device which can result in delamination of the layers or tearing of the graft.

Accordingly, it would be desirable to provide an improved intraluminal device, in particular, an ePTFE graft-stent composite device with improved radial strength that allows for the deployment of a stent and graft simultaneously with the stent already positioned along the graft such that the stent is free to move transversely along the longitudinal axis of the graft as the stent is radially expanded so that additional stress is not placed on the graft by the transverse motion generated by the stent as it expands.

SUMMARY OF THE INVENTION

In accordance with the present invention, an improved composite graft-stent device with transverse motion is provided. More particularly, the present invention is formed from two non thrombogenic tubes which are laminated or fused together in two or more positions with one or more stents disposed within the pocket formed therebetween. This composite device is then expanded to place it in intimate contact with the inner surface of the lumen in which it is positioned.

This composite device is preferably an implantable intraluminal device with a first porous elongate tube that has first and second opposed ends, an interior luminal surface and an exterior surface. A second porous elongate tube is disposed concentrically over the first tube which defines an elongate expandable prosthesis. The first tube is secured to the second tube in order to form a longitudinally extending pocket therebetween. A generally annular radially expandable member is disposed about the exterior surface of the first tube and is located within the pocket. Thus, the expandable member is longitudinally mobile within the pocket(s) formed between the first and second tubes. In the present invention, the first and second tubes are secured to each other by fusion or by lamination, although any generally known method in the art for such securement may be used.

In the present invention, when the member is expanded, there is a distortion along the width of the member, e.g., the width decreases as the member is expanded. The space defined by the pocket in which the stent is positioned is sufficient to allow the member to move transversely along the longitudinal axis of the pocket as the member expands radially. This space allows the member to radially expand without exerting force against the surfaces of the first and second tubes. Thus, the present invention significantly reduces the risk of tearing the graft or of delaminating one of its layers.

The member is preferably an expandable stent. The stent of the present invention is preferably fabricated out of a biocompatible metal. Most preferably, the stent is stainless steel, platinum, gold, nitinol, tantalum and alloys thereof.

The first and second tubes of the present invention are preferably fabricated out of a bio-compatible material. Most preferably, the first and second tubes are fabricated out of expanded polytetrafluoroethylene (ePTFE).

In the present invention, the first tube is secured to the second tube at locations that are adjacent to each of the ends of the tubes. In this way, a pocket is formed between the two secured locations. Alternatively, the fist tube may be secured to the second tube at a plurality of spaced apart locations. In this way, pockets are formed between each adjacent secured location. In yet another embodiment of the present invention, each of the pockets supports a single stent. Alternatively, each of the pockets may support a plurality of stents.

In the present invention, the device may be a balloon expandable device. Thus, by inflating a balloon catheter positioned within the lumen of the device, the device may be radially expanded.

The process of the present invention hereby incorporates by reference all of the limitations described above for the intraluminal implantable device. By way of summary, in the process of the invention an implantable intraluminal device is provided which includes a first porous elongate tube having first and second opposed ends, an interior luminal surface and an exterior surface. One or more radially expandable members is/are then radially disposed about the exterior surface of the first tube. A second porous elongate tube is then concentrically positioned over the first tube. The first tube is then secured to the second tube at spaced apart locations in order to form a longitudinally extending pocket between the first and second tubes. In this way, the expandable member is longitudinally movably confined within the pocket.

BRIEF DESCRIPTION OF THE DRAWINGS

The present invention can be further understood with reference to the following description in conjunction with the appended drawings, wherein like elements are provided with the same reference numbers. In the drawings.

DETAILED DESCRIPTION OF THE PREFERRED EMBODIMENT

Figure 1:
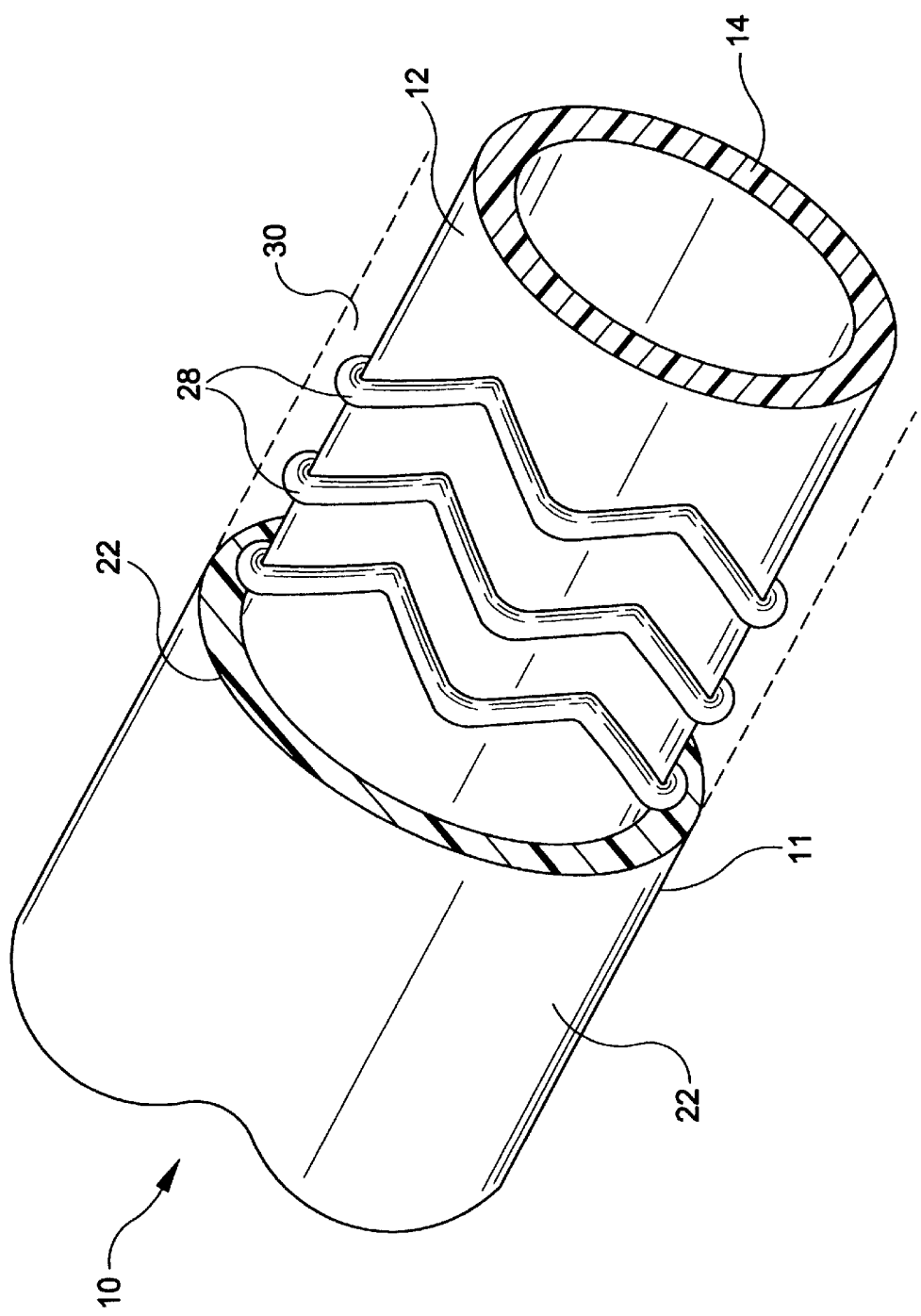
FIG. 1 is a perspective showing partially cut away, the graft-stent composite structure of the present invention.

Now turning to FIG. 1, the preferred embodiment of the graft-stent composite device 10 of the present invention is shown. This device 10 includes a composite multilayer graft 11 which is formed of an inner tube 12 and an outer tube 22 each preferably formed of expanded polytetrafluoroethylene (ePTFE). Although it is preferred that tubes 12 and 22 be made of ePTFE, any appropriate bio-compatible material, such as porous polyurethane, is also contemplated. Other potential materials for this application include DACRON, a proline mesh or the like. Ideally, the material should be inert and should not promote a significant amount of scar formation. Graft-stent composite device 10 further includes a plurality of spaced apart stents 28 positioned between inner tube 12 and outer tube 22. Stents 28, as will be described in further detail hereinbelow, are radially expandable to permit expansion of the graft-stent composite device 10.

Figure 2:
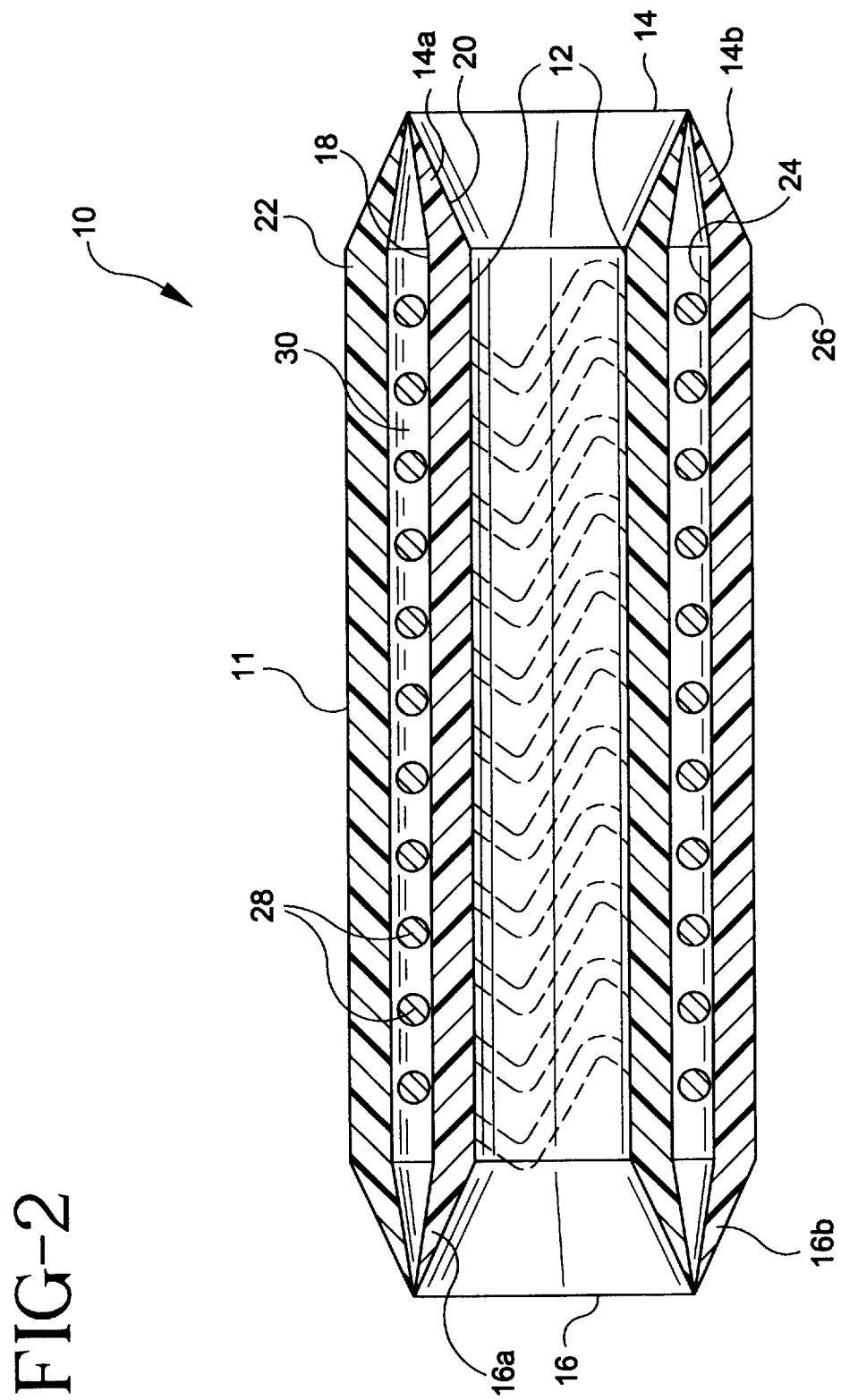
FIG. 2 is a longitudinal cross-section of the covered stent of FIG. 1.

Referring additionally to FIG. 2, composite multilayer graft 11 is an elongate member having first and second opposed ends 14 and 16, respectively. Tube 12 includes an exterior surface 18 and an interior luminal surface 20. Tube 22 has an interior surface 24 and an exterior vascular surface 26. Each tube 12, 22 includes respective ends 14a, 16a and 14b, 16b. Tube 22 is disposed concentrically over the exterior surface 18 of tube 12 to form composite multilayer graft 11.

The plurality of longitudinally spaced stents 28 are disposed between the exterior surface 18 of tube 12 and the interior surface 24 of tube 22 in a space or pocket 30 formed between the ends 14, 16 of composite multilayer graft 11. Stents 28 are transversely moveable along the longitudinal axis of composite multilayer graft 11 in pocket 30.

As partially shown in FIG. 2, first ends 14a and 14b and second ends 16a and 16b of first and second tubes 12 and 22 respectively are laminated together to form a single longitudinally extending pocket 30 for accommodating the plurality of stents 28 therein. Each stent 28 is typically placed over inner tube 12 prior to placement of outer tube 22 thereover. The stents 28 are positioned intermediate ends 14a, 16a thereof so that upon lamination of end 14b, 16b of outer tuber 22 to ends 14a, 16a of inner tuber 12, stents 28 will be resident in the pocket 30 formed therebetween. Although FIG. 2 shows the ends of tubes 12 and 22 laminated together, any appropriate method of securement, such as fusion, is contemplated.

Lamination or other securement of the inner tube 12 to outer tube 22 at ends 14 and 16 thereof assures that graft 11 functions as a single structure. Thus, once implanted there is no separation between the tubes. Upon expansion of the composite device 10, as will be described hereinbelow, the layers thereof formed by inner tube 12 and outer tube 22 do not separate. In this regard, movement of the stents 28 longitudinally along graft 11 is permitted by the appropriate formation of pocket 30. Such movement is achieved between the laminated ends 14 and 16 without risk of delamination of the ends and separation of the layers of graft 11.

Figure 3:
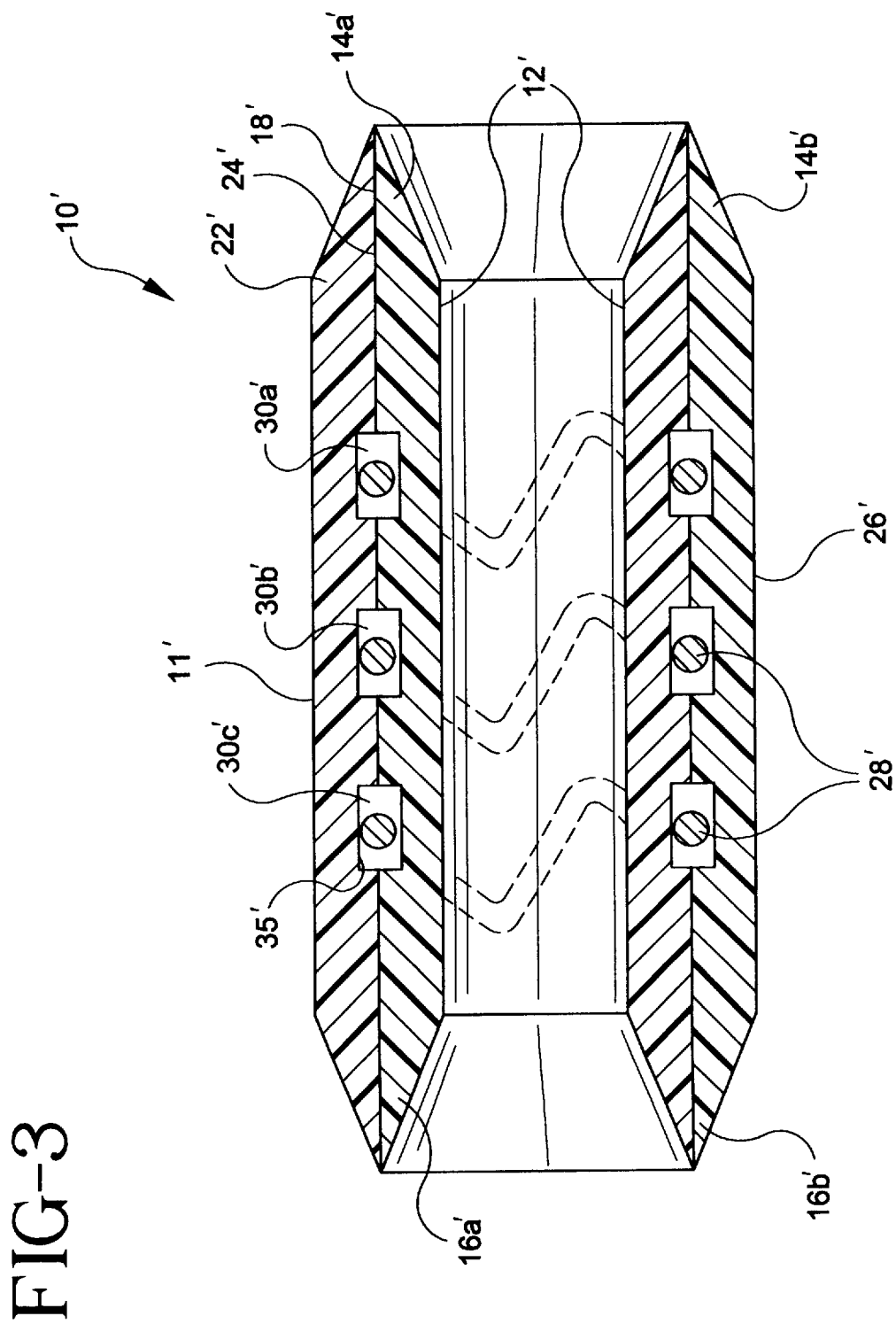
FIG. 3 is a longitudinal cross-section of another embodiment of the device of FIG. 1.

A further embodiment of the present invention is shown in FIG. 3. Graft 11' includes an inner tube 12' and outer tube 22' and plural stents 28 therebetween. A plurality of pockets 30a', 30b', and 30c', are formed in longitudinally spaced succession between tubes 12' and 22'. The pockets 30a'–30c' are formed by lamination of an exterior surface 18' of tube 12' to an interior surface 24' of tube 22' at a plurality of longitudinally spaced locations 35'. Within each pocket 30a'–30c' is disposed at least one stent 28. The pockets 30a'–30c' have sufficient longitudinal dimension so that the stents 28 held in each pocket may move longitudinally without delaminating the bonds 35' between tubes 12' and 22'. Thus, a plurality of expandable stents 28 may be longitudinally disposed about composite multilayer graft 11' of FIG. 3 without generating shear forces sufficient to delaminate or tear the layers of thereof. While 3 pockets 30a'–30c' are shown, it may be appreciated that any number of pockets and stents may be employed.

Figure 4:
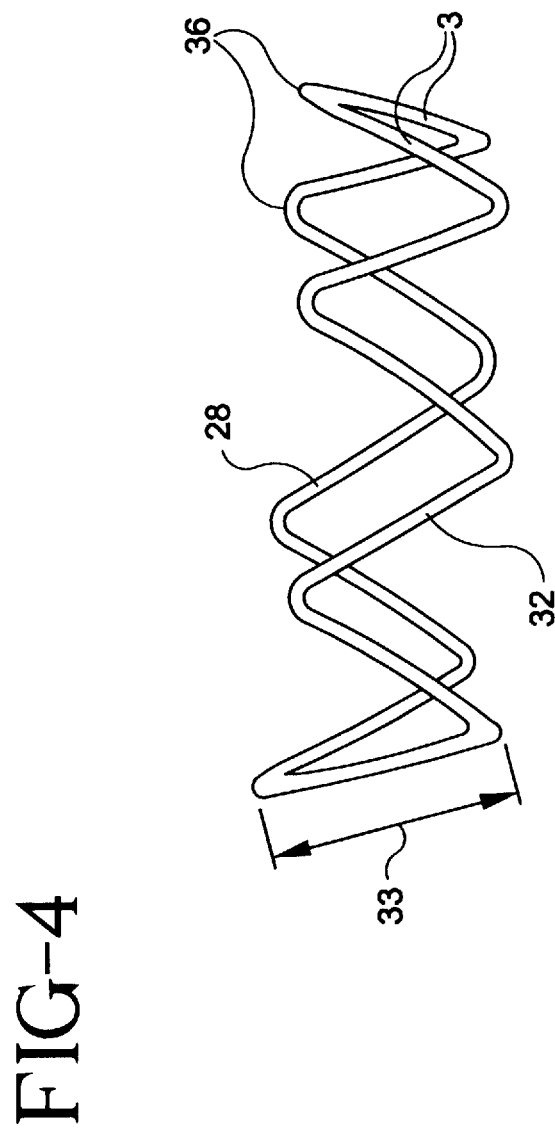
FIG. 4 is a side elevational view of a single stent utilized in the device of FIGS. 1–3.

In the present invention, any conventional radially expandable stent may be employed. With reference now more particularly to FIG. 4, it can be seen that each stent 28 of the preferred embodiment is generally annular and includes a plurality of angled straight sections 32 which are connected at bends 36. These stents 28 are radially expandable by, for example, the expansion of a balloon catheter exerting radial pressure on wire 32. As radial expansion of the stent 28 is achieved, the width 33 of the wire 32 decreases. The pocket 30 shown in FIG. 2 allows such radial expansion to occur without generation of shear forces on the first and second tubes 12 and 22 of the graft 11 as the stent 28 is free to move transversely within the pocket 30 as it expands. Thus, expansion of the composite multilayer graft 11 is accomplished without delamination of the layers of the graft or of a tear forming thereon.

Stents 28 of the invention are preferably manufactured out of a bio-compatible metal. Most preferably, the bio-compatible metal is stainless steel, platinum, gold, nitinol, tantalum and alloys thereof.

While the preferred embodiments of the invention are shown and described below, other embodiments that fall within the scope of the disclosure and appended claims are also contemplated. The invention being thus described, it will be obvious that the same may be varied in many ways. Such variations are not to be regarded as a departure from the spirit and scope of the invention and all such modifications are intended to be included within the scope of the following claims.

What is claimed is:

1. An implantable intraluminal device comprising:
    a first porous elongate tube having first and second opposed ends, said first tube having an exterior surface and an interior luminal surface;
    a second porous elongate tube disposed concentrically over said first tube, said first and second tubes defining an elongate expandable prosthesis;
    said first tube secured to said second tube to form a longitudinally extending pocket therebetween; and
    a generally annular radially expandable member disposed about the exterior surface of said first tube and located within said pocket, wherein said pocket has a longitudinal expanse greater than a longitudinal expanse of said radially expandable member, whereby said expandable member is longitudinally moveable within said pocket.

2. The implantable intraluminal device of claim 1, wherein said generally annular radially expandable member is a stent.

3. The implantable intraluminal device of claim 2, wherein said stent is a bio-compatible metal.

4. The implantable intraluminal device of claim 3, wherein said bio-compatible metal is selected from the group consisting of stainless steel, platinum, gold, nitinol, tantalum and alloys thereof.

5. The implantable intraluminal device of claim 1, wherein said first tube is secured to said second tube at secured locations adjacent each of said ends to form said pocket between said secured locations.

6. The implantable intraluminal device of claim 1, wherein said first tube is secured to said second tube at a plurality of longitudinally spaced locations to form one of said pockets between each adjacent secured location.

7. The implantable intraluminal device of claim 1, wherein each of said pockets support a single stent.

8. The implantable intraluminal device of claim 1, wherein each of said pockets support a plurality of stents.

9. The implantable intraluminal device of claim 1, wherein said first and second tubes are bio-compatible.

10. The implantable intraluminal device of claim 1, wherein said first and second tubes are fabricated of expanded polytetrafluoroethylene.

11. The implantable intraluminal device of claim 1, wherein said first and said second tubes are secured to each other by fusion.

12. The implantable intra-luminal device of claim 1, wherein said first and said second tubes are secured to each other by lamination.

13. The implantable intraluminal device of claim 1, wherein said device is a balloon expandable device.

14. A process for providing an implantable intraluminal device comprising:

a) providing a first porous tube having first and second opposed ends, said first tube having an exterior surface and an interior luminal surface;

b) disposing a generally annular radially expandable member about the exterior surface of said first tube;

c) positioning a second porous tube concentrically over said first tube and said expandable member;

d) securing said first tube to said second tube at spaced apart locations to form a longitudinally extending pocket between said first and second tubes wherein said pocket has a longitudinal expanse greater than a longitudinal expanse of said radially expandable member and said expandable member is longitudinally movably confined within said pocket.

15. The process of claim 14, wherein said generally annular radially expandable member is a stent.

16. The process of claim 14, wherein said securing step includes securing said first tube to said second tube at secured locations adjacent each of said ends and forming said pocket between said secured locations.

17. The process of claim 14, wherein said securing step further includes securing said first tube to said second tube at a plurality of longitudinally spaced secured locations and forming one of said pockets between each adjacent secured location.

18. The process of claim 14, wherein said securing step further includes supporting a single stent in each of said pockets.

19. The process of claim 14, wherein said securing step further includes supporting a plurality of stents in each of said pockets.

20. The process of claim 15, wherein said stent is a bio-compatible metal.

21. The process of claim 20, wherein said bio-compatible metal is selected from the group consisting of stainless steel, platinum, gold, nitinol, tantalum and alloys thereof.

22. The process of claim 14, wherein said first and second tubes are bio-compatible.

23. The process of claim 14, wherein said first and second tubes are expanded polytetrafluoroethylene.

24. The process of claim 14, wherein said securing step further includes fusing said first tube to said second tube at spaced apart locations to form a longitudinally extending pocket between said first and second tubes wherein said expandable member is longitudinally movably confined within said pocket.

25. The process of claim 14, wherein said securing step further includes laminating said first tube to said second tube at spaced apart locations to form a longitudinally extending pocket between said first and second tubes wherein said expandable member is longitudinally movably confined within said pocket.

* * * * *